United States Patent
Castañedo Cancio et al.

(12) 
(10) Patent No.: US 6,316,014 B1
(45) Date of Patent: Nov. 13, 2001

(54) MICROCIDE COMPOSITION

(75) Inventors: Nilo Ramón Castañedo Cancio; Grisell Diaz Martinez; Alain Ramirez Dieǵuez; Esther Lilia Martin Triana, all of Santa Clara; Eloisa Salazar Yera, Sague la Grande; Mirtha Maira González Bedia, Santa Clara; Rosa Margarita Machado Rodríguez, Santa Clara; Carlos Manuel González Lorenzo, Santa Clara; Madaysi de la Caridad Cueto Sánchez, Santa Clara, all of (CU)

(73) Assignee: Centro de Bioactivos Quimicos (CBQ) (CU)

( * ) Notice: Subject to any disclaimer, the term of this patent is extended or adjusted under 35 U.S.C. 154(b) by 0 days.

(21) Appl. No.: 09/214,075

(22) PCT Filed: Jan. 17, 1997

(86) PCT No.: PCT/CU97/00003

§ 371 Date: Aug. 10, 1999

§ 102(e) Date: Aug. 10, 1999

(87) PCT Pub. No.: WO97/49283

PCT Pub. Date: Dec. 31, 1997

(30) Foreign Application Priority Data

Jun. 21, 1996 (CU) .......................................... 57/96

(51) Int. Cl.[7] .................................................. A01N 25/08
(52) U.S. Cl. .......................... 424/405; 424/409; 514/471; 523/122; 523/123
(58) Field of Search ...................... 504/115, 294; 514/461, 471; 424/405, 409; 523/122, 123

(56) References Cited

U.S. PATENT DOCUMENTS

| | | | | |
|---|---|---|---|---|
| 4,017,627 | * | 4/1977 | Styrm | 424/258 |
| 4,965,254 | * | 10/1990 | Anderson et al. | 514/89 |

FOREIGN PATENT DOCUMENTS

| | | |
|---|---|---|
| 0 687 516 A | 10/1995 | (EP) . |
| 57 038703 A | 3/1982 | (JP) . |
| 60 146893 A | 8/1985 | (JP) . |
| 60 248648 A | 12/1985 | (JP) . |
| WO 89 11793 | 12/1989 | (WO) . |

* cited by examiner

Primary Examiner—Neil S. Levy
(74) Attorney, Agent, or Firm—Lackenbach Siegel

(57) ABSTRACT

A microcidal composition consisting of a water-soluble polymer and the active principle 1-(5-bromophur-2-yl)-2-bromo-2-nitroethene is provided to be used as chemical sterilizer of culture media for the control of bacterial and fungal contaminants.

This technical solution, even can be used for the sterilization of solid and liquid culture media, is particularly useful in the production of "in vitro" cultivated plants, and surprisingly was found that its utilization can substitute completely the previous process of sterilization that this media require and even more, the addition of the necessary hormones in the rootage process of "in vitro" plants of crops.

21 Claims, No Drawings

MICROCIDE COMPOSITION

TECHNICAL SECTOR

The present invention is related to the branch of Microbiology and in particular with a microcidal composition which contains as active principle 1-(5-bromophur-2-yl)-2-bromo-2-nitroethene, which is used as chemical sterilizer of culture media for the control of bacterial and fungal contaminants.

PRIOR ART

The contamination of culture media for example, in the production of plants cultivated "in vitro", cause substantial losses to the whole process since the autoclave only eliminates at-the-moment pollution. In some cases different antibiotics, e.g., Cefotaxim, Novobiocin, and Dihydrostreptomycin have been used to prevent contamination without satisfactory results.

The compound 1-(5-bromophur-2-yl)-2-bromo-2-nitroethenehas been previously described (Z. N. Nazarova, 1972. "Synthesis of some furylnitroolefins with potential biological activity, Khim. Farm. Zh. 6(10,) pp. 5–8 and Z. N. Nazarova et al, 1972." Physicochemical properties and reactivity of furylnitroolefins, Zh, Org. Khim. 8 (2), pp. 404–11) and it is also known as a powerful agent with antibacterial and antifungal activities (European patent application No. EP-A 0 678 516).

DISCLOSURE OF THE INVENTION

The present invention provides a microcidal composition which can be advantageously used for the control of contaminants in culture media, such as bacterial or fungal contaminants.

This technical solution, even can be used for the sterilization of solid and liquid culture media, is particularly useful in the production of "in viro" cultivated plants, and surprisingly was found that its utilization can substitute completely the previous process of sterilization that this media require and even more, the addition of the necessary hormones in the rootage process of in vitro plants of crops.

The main limitation against the use of this active principle as sterilizer agent in solid media has been its close-to-null water solubility and the also reduced dissolution rate in an aqueous medium. A possible solution to this problem could be solid dispersions, which allow for a decrease of the particle size to molecular level.

The method proposed in the present provides a microcidal composition which contains as active principle 1-(5-bromophur-2-yl)-2-bromo-2-nitroethene as sterilizing agent and consists in dispersion by fusion or co-precipitation of this compound in a physiologically inert matrix and easily soluble in water, which is formed by a high molecular weight polyethylene glycol and other polymers.

In order to carry out the dispersion by fusion of the 1-(5-bromophur-2-yl)-2-bromo-2-nitroethene, the selection of the manufacture methods and temperature parameters, as well as that of stirring times were based on the melting point and thermal stability of the active principle and the polymer elected.

The compound 1-(5-bromophur-2-yl)-2-bromo-2-nitroethene is melted without decomposition at a temperature of 89–90° C. and is thermally stable up to 110° C.

However, the elaboration of solid disperse systems of the active principle with polymers whose melting points are higher than 110° C. affect the active principle thermal stability and, therefore, it is recommended the co-precipitation method in a solvent.

In order to carry out the dispersion by fusion of the 1-(5-bromophur-2-yl)2-bromo-2-nitroethene, physical mixture of the active principle and PEG-6000 in a ration from 1:20 to 1:1 heats up to fusion at the temperature of 60–80° C. and remains under constant stirring for 15 minutes until an entire homogeneity of the melting is reached. Then, the mixture melted is poured and spread as a thin layer on refrigerated stainless steel plates, thus ensuring the speed of the solidification process. The solid obtained is grinded in mills and screened at a particle size smaller than 0.2 mm.

The melting point range of solid dispersions of the active principle and PEG-6000 varies with the composition of the mixture, being 53–540° C. for the solid dispersion by fusion dispersion at 30% whose composition coincides with the eutectic composition of the binary system active principle-PEG-6000.

In order to obtain a dispersion by co-precipitation of 1-(5-bromophur-2-yl)-2-bromo-2-nitroethene the mixture of the active principle and the polymer in ratios from 1:20 to 1:1 is dissolved in a polar solvent heated in an interval of 10–60 minutes at a temperature ranging between 40 and 60° C. Then, it is vacuumrotoevaporated controlling temperature from 40–80° C. The solid thus obtained is grinded in a mill and screened at a particle size smaller than 0.2 mm For the elaboration of liquid culture medium containing 1-(5-bromophur-2-yl)-2-bromo-2-nitroethene, the compound is included in a aqueous formulation using tensioactive compounds such as Solutol IIS-15 and Cremophor, among other compounds. This compositions has been prepared looking for a good stability and solubility of the compound and in a concentration that does not affect adversely the organisms which are cultivated in said medium.

Once they are obtained stable compositions containing 1-(5-bromophur-2-yl)-2-bromo-2-nitroethene using the methods described above, different assays were carry out in order to know the optimum dose, particularly using the compound as sterilizer agent of solid culture media used for the propagation of "in vitro" cultivated plants. Phytoxicity was evaluated considering necrosis, chlorosis, multiplication coefficient and junction-to-junction distance (for potatoes), For those cultures studied (banana, potato and sugar cane), the optimum dose of the 1-(5-bromophur-2-yl)-2-bromo-2-nitroethene was in a range between 30 and 45 □g/ml.

The following examples are directed to show the invention but not to limit its scope.

EXAMPLE 1

INFLUENCE OF TEMPERATURE AND TIME ON THE PURITY OF THE SOLID DISPERSION OBTAINED BY THE FUSION METHOD.

A study of the influence of temperature and time an the purity of the composition containing 1-(5-bromophur-2-yl)-2-bromo-2-nitroethene obtained by obtained by the fusion method was carried cut.

It was observed that that the purity of the active principle in the obtained solid dispersion depends on the temperature and the stirring time used.

TABLE 1 shows the 1-(5-bromophur-2-yl)-2-bromo-2-nitroethene purity percentages obtained by solid dispersion of this compound in PEG 6000 (30:70), using melting temperatures between 80° C. and 120° C. and stirring times between 15 and 60 minutes.

The study in all cases was carried out as it is described below.

For a temperature of 80° C. and a stirring time of 15 minutes, the physic mix of 1-(5-bromophur-2-yl)-2-bromo-2-nitroethene and PEG 6000 (30:70) is heated up to melting and kept under constant stirring during 15 minutes up to achieve the complete homogeneity of the melted. The melted mix is poured as a thin layer on cooled sheets of stainless steel. The solid thus obtained is grinded in a mill and screened at a particle smaller than 0.2 mm.

The purity of the active substance in the dispersion obtained under the above conditions, determined by Gas Chromatography, was about 99,89%.

TABLE 1

Influence of temperature and time on the purity of the solid dispersion obtained by the fusion method.

| Temperature (° C.) | Time (min.) | Purity (%) |
|---|---|---|
| 80 | 15 | 99.89 |
| 80 | 30 | 99.61 |
| 80 | 60 | 99.22 |
| 100 | 15 | 99.00 |
| 100 | 30 | 98.35 |
| 100 | 60 | 97.21 |
| 120 | 15 | 90.58 |
| 120 | 30 | 78.19 |
| 120 | 60 | 63.85 |

EXAMPLE 2

DETERMINATION OF DISOLUTION PROPERTIES OF THE 1-(5-bromophur-2-yl)-2-bromo-nitroethene AFTER THE PROCESSES OF DISPERSION BY FUSION OR BY CO-PRECIPITATION.

Important in the obtainment of aqueous homogeneous solution/suspensions of the active principle are the dissolution properties thereof.

TABLE 2 establishes a comparison among the dissolution rates of the active principle with humectant, micronized, and standard particle sizes and using a solid dispersion with PEG6000 at 30%. It may be noticed how the active principle properties improve significantly thus ensuring the rate and homogeneity of its distribution in the culture medium.

TABLE 2

Dissolution rate evaluation of 1-(5-bromophur-2-yl)-2-bromo-2-nitroethene presented in the culture medium in different forms.

| | Times | | |
|---|---|---|---|
| | 10% | 50% | 90% |
| Active principle particle size: 0.1–0.2 mm | <1 h | <12 h | <48 h |
| Micronized active principle | <30 min. | <6 h | <24 h |
| Humectant active principle | <15 min. | <3 h | <6 h |
| Solid dispersion Active Principle-PEG 6000 at 30% | <5 s | <10 s | <15 s |

EXAMPLE 3

DETERMINATION OF THE CHEMICAL STABILITY OF THE ACTIVE PRINCIPLE DISPERSED/DILUTED IN PEG.

The chemical stability of the active principle dissolved-dispersed in polyethylene glycol has been studied with the use of Gas Chromatography as the analytical technique for the quantification thereof.

A chemical stability study lasting 385 days proves the no existence of decomposition.

TABLE 3

Evaluation of the shelf chemical stability of solid dispersion in PEG-6000 at 30% by Gas Chromatography.

| Time (days) | 0 | 60 | 90 | 120 | 150 | 210 | 306 | 385 |
|---|---|---|---|---|---|---|---|---|
| % Active Principle | 28.6 | 28.9 | 29.9 | 28.8 | 29.0 | 29.0 | 29.3 | 28.9 |

EXAMPLE 4

ACTIVITY OF A FORMULATION CONTAINING 1-(5-bromophur-2-yl)-2-bromo-2-nitroethene ON SELECTED MICROORGANISMS.

Following the completion of formulation studies an in vitro assay was conducted to determine the product activity against agricultural pathogens and contaminating microorganisms present in the process of production of "in vitro" cultivated plants. The study of bacteria was carried out under the serial dilution method in tubes (Bailey, W. R. and Scott, E. S. Diagnostic Microbiology $4^{th}$ Edition, pp. 313–329. The C. V. Mosby Co. St. Louis, 1974) as modified by E. Silveira (Silveira E. et al, Determinacion de la minima concentracion inhibitoria (M.C.I.) de sustancias bioactivas, Boletin Cientifico ISCM IV (2), 1986), and the action against fungi was evaluated through the diameter growth of the colony (Casadens II: Metodo de investigaciones fitopatologicas. Instituto Iberoamericano de Cooperacion para la Agricultura. San Jose de Costa Rica, 1985).

The concentrations used for evaluating the bioactive product behavior were 1 to 10 μg/ml. The culture medium, temperature and interval of incubation were adjusted to the conditions and characteristics of the microorganism under assay.

The $LD_{-50}$ was calculated in μg/ml under Probit's method (Finney D. J. Probit analysis. $3^{rd}$ Ed. Cambridge University Press. 1971).

The results obtained from this study are shown in TABLE 4.

TABLE 4

In vitro tests conducted with relevant LD50 value against the following agriculturally important microorganisms

| | | LD/50 ug/ml |
|---|---|---|
| 1.1. | Gram Negative Bacteria | |
| | 1.1.1. Pseudomonadaceae family | |
| | *Xanthomonas vesicatoria* | 15–25 |
| | *Pseudomona cichorii* | 15–25 |
| | 1.1.2. Enterobaceriaceae family | |
| | *Erwinia Chrysanthemi* | 20–30 |
| | Gram Negative Bacillus (bioplants contaminant) | 20–30 |
| 1.2. | Gram Positive Bacteria | |
| | 1.2.1. Bacillaceae family | |
| | Gram Negative Bacillus (bioplants contaminant) | 20–30 |
| 2.1. | Monomorphic yeastlike fungi | |
| | 2.1.1 - Dematiaceae family | |

TABLE 4-continued

In vitro tests conducted with relevant LD50 value against the following agriculturally important microorganisms

| | LD/50 ug/ml |
|---|---|
| *Alternaria porri* | 1.9–2.5 |
| Alternaria solani | 1.5–2.3 |
| 2.1.2. Pythiaceae family | |
| *Phythophtom panesitica* | 1.9–3.2 |
| 2.1.3. Tuberculariaceae family | |
| *Fusarium oxysporium* | 10.4–11.5 |
| 2.1.4. Melanconiaceae family | |
| *Colletotrichum gloesporioides* | 1.0–1.8 |
| 2.1.5. Estilbaceae family | |
| *Sclerotium rolfii* | 0.2–0.9 |
| 2.1.6. Dothideaceae family | |
| *Mycosphaerelia mussicola* | 3.0–7.0 |
| *Mycosphaerella fijiensis* | 3.0–7.0 |
| 2.1.7. Moniliaceae family | |
| *Aspergillus niger* | 15.5–17.5 |
| Penicillium sp | 15.6–18.5 |
| Cladosporium sp | 10.6–11.4 |

EXAMPLE 5

DETERMINATION OF THE ACTION OF 1-(5-bromophur-2-yl)-2-bromo-2-nitroethene ON CULTURE MEDIA USED IN THE PRODUCTION OF "IN VITRO" CULTIVATED PLANTS.

After proving the active principle in vitro action against fungal and bacterial contaminants of the vitro planting of bananas, potatoes and sugar cane we proceeded as follows:

An effective washout of the flasks and lids to be used in the production of in vitro plants was conducted using detergent, rinsing them with sufficient water and to then submerging the bottles in a sodium hypochlorite solution at 0.5% for a time interval never smaller than 3 minutes. Afterwards, the flasks are placed upside down and they should be used totally dry before 24 hours.

Once the culture medium is prepared and reaches a temperature of approximately 60–80° C. it is added the necessary weight of the formulation to obtain a concentration of 35 µg/ml and, then the volume required is poured into each of the flasks proceeding to the planting procedure after 24 hours.

This concentration is selected on the basis of its effectivity and lack of phytotoxic effects in the culture media studied.

The range assayed was 1–50 µg/ml. The behavior of in vitro cultures of bananas, potatoes, and sugar cane was evaluated after 72 hours and during the period required for its culture in order to carry out the following sub-culture in the multiplication medium. Such a study was conducted in the rootage culture medium.

Phytotoxicity was evaluated considering necrosis, chlorosis, multiplication coefficient, and junction-to-junction distances (for potatoes). The optimum dose in the three cultures studied was about 30 and 45 µg/ml.

Two scaleup studies were conducted on a Musa sp. culture in the multiplication phase. The death rate percentage during the three assays was 0.81% for the scaleups conducted adding the active principle and 1% for the standard method.

The results obtained in this study are shown in TABLE 5.

TABLE 5

Action of the solid dispersion containing 1-(5-bromophur-2-yl)-2-bromo-2-nitroethene against contaminating organisms in culture media used for the production of vitro-plants of Musa sp.

| Scaleup No. | Clone | Explant No. | % of contamination < 11 days | % of contamination > 11 days |
|---|---|---|---|---|
| 1 | Gran nayne | 8240 | 1.72 | 4.67 |
| 2 | FHIA-03 | 15000 | 3.92 | 7.26 |
| Witness | FHIA-03 | 15000 | 4.00 | 5.80 |

Out of these assays it possible to infer that contaminations behaved similarly to those of the witness used with physical sterilization of the culture medium using an autoclave and that they started increasing as from the eleventh day. In addition, an increment of the multiplication coefficient was noticed when working with the chemical sterilizer, The rootage medium without autoclaves nor addition of hormones stimulating the induction of roots showed a visible effect superior to that of the standard method with the appearance of stronger and more abundant roots in a shorter period of time. The contamination percentage detected was significant.

TABLE 6

Action of the solid dispersion containing 1-(5-bromophur-2-yl)-2-bromo-2-nitroethene on the development of "in vitro" plants.

| Scaleup No. | Clone | Explant No. | Multiplication coeffcient |
|---|---|---|---|
| 1 | Gran nayne | 8240 | 3.87 |
| 2 | FHIA-03 | 15000 | 4.03 |
| Witness | FHIA-03 | 15000 | 3.0 |

Two scaleup studies were conducted on a Musa sp. culture in the multiplication phase.

In addition, an assay was conducted on Muse sp. With clones Gran nayne and FHIA-03 in rootage culture medium without adding root-inducing hormones (A.I.A.). Both clones behaved better in the variants where a chemical sterilization was carried out since a larger amount of stronger roots was observed after 5 days, while the witness with the standard procedure only showed a small radical development in the same period.

What is claimed is:

1. A microbicidal composition comprising 1-(5-bromophur-2-yl)-2-bromo-2-nitroethene and a water-soluble polymer.

2. The microbicidal composition of claim 1, wherein the water soluble polymer is a high molecular weight polyethylene glycol.

3. The microbicidal composition of claim 2, wherein the high molecular weight polyethylene glycol has a molecular weight between 6000 and 20000.

4. The microbicidal composition of claim 3 wherein the high molecular weight polyethylene glycol is PEG 6000.

5. A method for controlling contamination of culture media comprising the step of sterilizing the culture media with a microbicidal composition having 1-(5-bromophur-2-yl)-2-bromo-2-nitroethene and a water soluble polymer.

6. The method according to claim 5 wherein the water soluble polymer is high molecular weight polyethylene glycol.

7. A process for the production of in-vitro cultivated plants in a culture medium comprising the step of adding a composition having 1-(5-bromophur-2-yl)-2-bromo-2-nitroethene and a water soluble polymer as rootage agent in the culture media.

8. A method for sterilization of culture media used in the production of "in vitro" cultivated plants comprising the step of adding a composition having 1-(5-bromophur-2-yl)-2-bromo-2-nitroethene into the culture media.

9. A method for obtainment of a microcidal composition comprising the step of dispersing an amount of 1-(5-bromofur-2-yl)-2-bromo-2-nitroethene in a water soluble polymer.

10. The method according to claim 9 wherein the amount of 1-(5-bromofur-2-yl)-2-bromo-2-nitroethene is dispersed in the water soluble polymer by fusion.

11. The method according to claim 9 wherein the amount of 1-(5-bromofur-2-yl)-2-bromo-2-nitroethene is dispersed in the water soluble polymer by co-precipitation.

12. The method according to claim 8, wherein the composition is used at the same time as a rootage agent in the culture media.

13. The method according to claim 8 wherein the 1-(5-bromophur-2-yl)-2-bromo-2-nitroethene is present in the composition in an amount of about 30 and 45 $\mu$m/ml.

14. A culture media comprising 1-(5-bromofur-2-yl)-2-bromo-2-nitroethene as a sterilizing and rootage agent.

15. The method according to claim 9 comprising the steps of: preparing a mixture of 1-(5-bromofur-2-yl)-2-bromo-2-nitroethene and PEG-6000;

heating the mixture to a temperature between about 60° C. and about 80° C.;

stirring the mixture until homogeneity of melting is reached;

pouring the melted mixture over a solidification medium;

spreading the melted mixture as a thin layer over the solidification medium; and obtaining a solid.

16. The method according to claim 9 comprising the steps of:

forming a mixture by dissolving 1-(5-bromofur-2-yl)-2-bromo-2-nitroethene and a water soluble polymer in a solvent, vacuum-rotoevaporating the solvent; and obtaining a solid.

17. A method according to claims 16 wherein the solvent is a polar solvent.

18. A method according to claim 17 wherein the polar solvent is selected from the group consisting of: ethanol, chloroform, methanol, isopropylic alcohol, and mixtures thereof.

19. The method according to claim 7 wherein the 1-(5-bromophur-2-yl)-2-bromo-2-nitroethene is present in the composition in an amount of about 30 and 45 $\mu$m/ml.

20. The method according to claim 7 wherein the water soluble polymer is a high molecular weight polyethylene glycol.

21. The process according to claim 8 wherein the water soluble polymer is a high molecular weight polyethylene glycol.

* * * * *